United States Patent [19]
Schreiber

[11] Patent Number: 5,171,529
[45] Date of Patent: Dec. 15, 1992

[54] OCCULT BLOOD TESTING DEVICE

[76] Inventor: Robert Schreiber, 527 Fey Rd., Chestertown, Md. 21620

[21] Appl. No.: 825,565

[22] Filed: Jan. 24, 1992

[51] Int. Cl.$^5$ .................... G01N 33/48; G01N 33/72
[52] U.S. Cl. .................... 422/58; 422/56; 422/61; 435/805; 436/60; 436/169
[58] Field of Search .................... 422/58, 61, 56, 55; 436/66, 169; 435/805, 299, 300, 301

[56] References Cited

U.S. PATENT DOCUMENTS

| | | | |
|---|---|---|---|
| 3,996,006 | 12/1976 | Pagano | 422/58 |
| 4,092,120 | 5/1978 | Suovaniemi et al. | 422/58 X |
| 4,225,557 | 9/1980 | Hartl et al. | 422/56 |
| 4,273,741 | 6/1981 | Levine | 422/56 |
| 4,365,970 | 12/1982 | Lawrence et al. | 436/66 |
| 4,486,536 | 12/1984 | Baker et al. | 436/66 |
| 4,582,658 | 4/1986 | Guadagno et al. | 436/66 X |
| 4,645,743 | 2/1987 | Baker et al. | 436/66 |
| 4,742,002 | 5/1988 | Guadagno | 435/28 |
| 4,789,629 | 12/1988 | Baker et al. | 435/7 |
| 4,804,518 | 2/1989 | Levine et al. | 422/56 |
| 4,808,379 | 2/1989 | Wardlaw et al. | 422/56 |
| 5,064,766 | 11/1991 | Wardlaw et al. | 436/66 |
| 5,081,040 | 1/1992 | Patel et al. | 436/66 |
| 5,100,619 | 3/1992 | Baker et al. | 422/58 |
| 5,106,582 | 4/1992 | Baker | 422/58 |

*Primary Examiner*—James C. Housel
*Assistant Examiner*—Long V. Le
*Attorney, Agent, or Firm*—Connolly and Hutz

[57] ABSTRACT

A testing device for determining the presence of occult blood in fecal matter has a primary support sheet with several window openings therein for receiving fecal matter. Guaiac test paper positioned on top of the support sheet covers the window openings. A strip of flexible opaque material is folded in two over the test paper, and a portion of the flexible material forms a pull tab which extends outwardly and away from the support sheet. An absorbent pad impregnated with hydrogen peroxide/alcohol is secured on top of the layered strip material, and a seal wrap covers the layers of strip material and the absorbent pad. Pulling the tab away from the primary support sheet draws the absorbent pad under the layers of flexible material and across the test paper to thereby moisten the paper covering the window openings and react with the guaiac in the test paper to turn the paper blue when blood is present in the fecal matter.

12 Claims, 2 Drawing Sheets

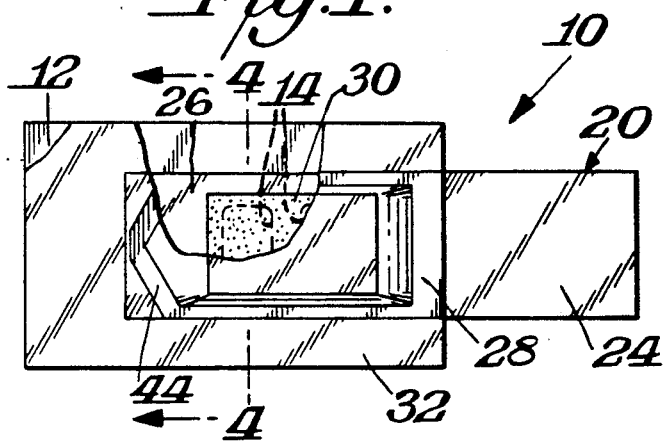
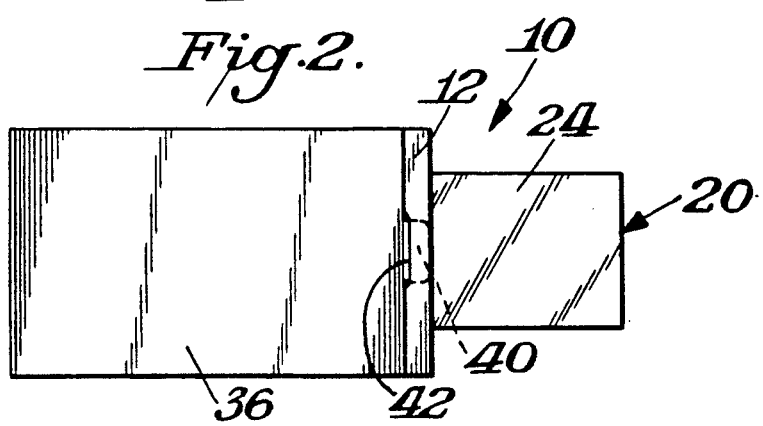
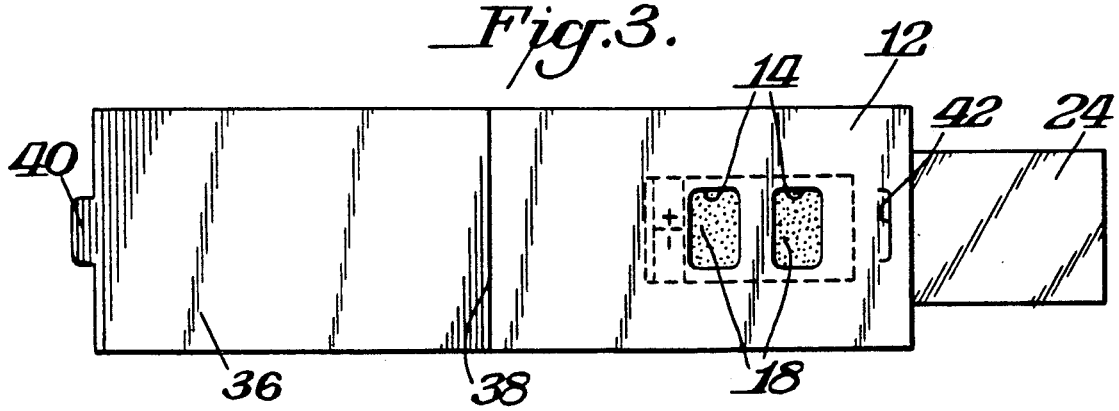
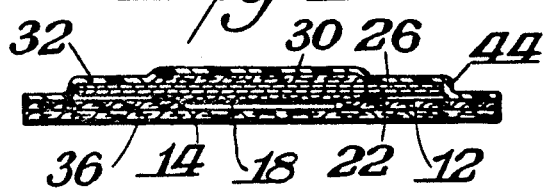

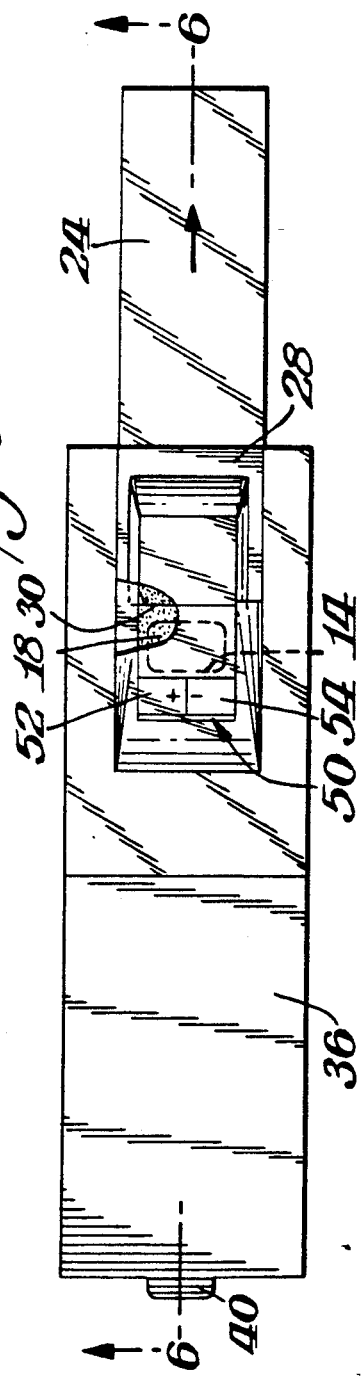
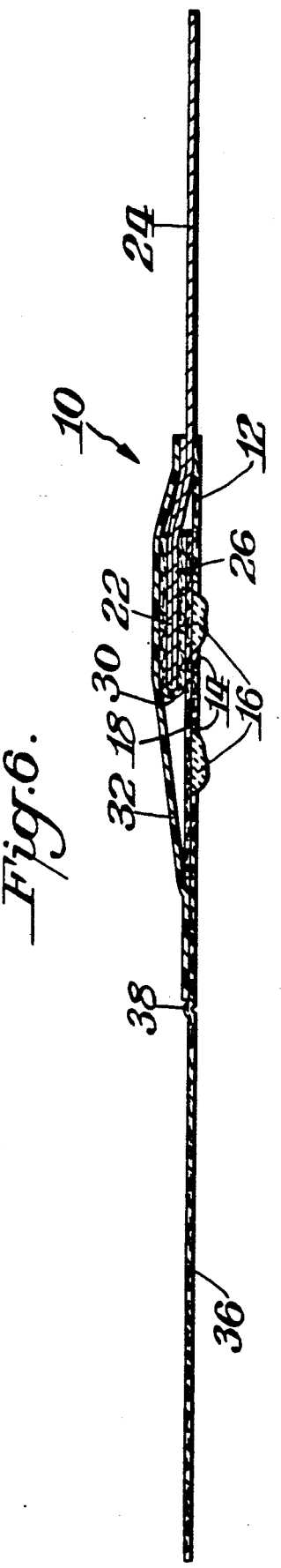

OCCULT BLOOD TESTING DEVICE

BACKGROUND OF THE INVENTION

The present invention relates to a testing device for determining the presence of occult blood in fecal matter, and more particularly to such a device for use in the home.

Over 100,000 persons in the United States are affected by cancer of the colon and rectum per year, occurring equally in both the men and women. When the number of colorectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90% of those persons affected by the disease. If, however, the disease is not detected until the later stages, the cure rate drops drastically to 25% or less. Thus, early detection of the disease is critical to successful treatment of digestive tract cancer.

Most, but not all cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Most advance cancers cause gross bleeding.

It is known that digestive tract cancers in the early stages also tend to bleed, giving rise to occult (hidden) blood in the fecal matter. Test equipment and test procedures have been developed for use by physicians in testing for the presence of occult blood in fecal matter. One of the most successful tests is manufactured and sold by Smith Kline Diagnostics, a division of Smith Kline Instruments, Inc. of Sunnyvale, Calif. under the trademark Hemoccult and disclosed in U.S. Pat. No. 3,996,006 issued to J. F. Pagano. Briefly, the Pagano test employs an absorbent paper impregnated with a guaiac reagent and encased in a special test slide having openable flaps on both sides of the test slide. To use the Pagano test slide, the physician or a lab technician must obtain a sample of fecal matter, smear it onto the guaiac impregnated paper by opening the panel on one side of the test slide, and thereafter close the panel. A panel on the opposite side of the test slide is then opened and a nonaqueous developing agent is applied to the guaiac impregnated paper. If occult blood is present in the fecal matter smeared on the opposite side of the paper, the guaiac reaction will dye the paper blue, providing a positive indication of the presence of blood in the fecal matter.

Although the Pagano test is excellent for use by physicians in their offices and by diagnostic laboratories, it is not the type of test which is readily adaptable for use by the ordinary person. It is cumbersome and requires too many manipulative steps, particularly the step of applying the nonaqueous developing agent to the guaiac impregnated paper.

SUMMARY OF THE INVENTION

Accordingly, it is an object of the present invention to provide a simple, highly reliable, and easy to use testing device, particularly suited for use in the home, for determining the presence of occult blood in fecal matter.

In accordance with the present invention a testing device for determining the presence of occult blood in fecal matter comprises a primary support sheet having top and bottom surfaces with at least one window opening therein for receiving fecal matter. A strip of test paper located on the top surface of the support sheet covers the window opening therein. A strip of flexible material is folded in two over the test paper and includes a first layer portion next to the test paper, a pull tab portion extending outwardly and away from the first layer portion past the support sheet, and a second layer portion next to the first layer portion terminating at a free inside end. An absorbent pad impregnated with reaction liquid is secured to the strip of flexible material on top of the second layer portion, and a transparent seal wrap covers the layers of strip material and the absorbent pad. The seal wrap is secured to the top surface of the primary support sheet as well as the inside free end of the strip material. Pulling the tab portion away from the primary support sheet draws the absorbent pad under the first and second layers of flexible material and across the test paper to thereby moisten the paper covering the window opening and react with the test paper to turn the paper a predetermined color when blood is present in the fecal matter.

Preferably the test paper includes gum guaiac resin and the reaction liquid includes hydrogen peroxide/alcohol. When these substances are combined in the presence of blood the guaiac turns the test paper blue.

Preferably the testing device includes an opaque back flap cover hingedly connected to the primary support sheet for covering the window opening before using the device. Releasable locking means is provided on the back flap cover and the primary support sheet for releasably locking them together before using the device. Moreover, it is preferred that the primary support sheet and the back flap cover be fabricated of cardboard.

The strip of flexible material is preferably opaque, and aluminum foil is particularly suitable for that purpose. Also, the primary support sheet may include a pair of spaced apart window openings with the test paper covering each of the openings.

The testing device may include a monitor which produces a visual indication that the device is functioning in a proper manner.

BRIEF DESCRIPTION OF THE DRAWINGS

Novel features and advantages of the present invention in addition to those mentioned above will become readily apparent to those of ordinary skill in the art from a reading of the following detailed description in conjunction with the accompanying drawings wherein similar reference characters refer to similar parts and in which:

FIG. 1 is a top plan view of an occult blood testing device with portions broken away to show interior details, according to the present invention;

FIG. 2 is a bottom plan view of the occult blood testing device of FIG. 1 illustrating the back flap cover in its latched and closed position;

FIG. 3 is a bottom plan view similar to FIG. 2 but illustrating the back flap cover in its unlatched and open position;

FIG. 4 is a cross-sectional view taken along line 4—4 of FIG. 1;

FIG. 5 is an enlarged top plan view similar to FIG. 1 but illustrating the tab being pulled to draw the absorbent pad across the test paper; and FIG. 6 is a longitudinal sectional view taken along line 6—6 of FIG. 5.

DETAILED DESCRIPTION OF THE INVENTION

Referring in more particularity to the drawing, the various figures illustrate a testing device 10 for determining the presence of occult blood in fecal matter. The device is simple in nature and easy to use in the privacy of one's home.

Testing device 10 includes a primary support sheet 12 having top and bottom surfaces with a pair of window openings 14 therein for receiving fecal matter 16. A sheet of test paper 18 is positioned on the top surface of the primary support sheet 12 so that it covers the window openings 14. Adhesive may be applied to a boundary edge portion of the test paper to secure it in place over the window openings.

A strip of flexible material 20 is folded in two over the test paper 18, as shown best in FIGS. 4 and 6. The strip material includes a first layer portion 22 on top of the test paper and a pull tab portion 24 which extends outwardly and away from the first layer portion 22 past the primary support sheet 12. The first layer of strip material is integral with a second layer portion 26 positioned on top of the first layer. The second layer portion terminates in a free inside end 28.

An absorbent pad 30 impregnated with reaction liquid is secured to the strip of flexible material 20 on top of the second layer portion 26, and a transparent seal wrap 32 covers the layers of the strip material 22, 26 and the absorbent pad 30. The seal wrap 32 is secured to the top surface of the primary support sheet 12 and the inside free end 28 of the strip material.

Pulling the tab portion 24 away from the primary support sheet 12 draws the absorbent pad 30 under the first and second layers 22, 26 of flexible material 20 and across the test paper 18 to thereby moisten the test paper covering the window openings 14 with the reaction liquid held by the absorbent pad. This liquid reacts with the test paper to turn the paper a predetermined color when blood is present in the fecal matter applied to the test paper on the bottom surface of the primary support sheet.

The test paper 18 may include gum guaiac resin and the reaction liquid of the absorbent pad 30 may include hydrogen peroxide/alcohol, for example 6% hydrogen peroxide, 70% ethanol, and 24% water. The alcohol puts the gum guaiac in solution and the hydrogen peroxide reacts with the gum guaiac in the presence of a catalase (blood in this case) which turns the test paper blue to thereby indicate the presence of occult blood in the fecal matter applied to the test paper.

A back flap cover 36 connected to the primary support sheet 12 by an integral hinge 38 functions to cover the window openings 14 before the device 10 is used. This is particularly important since many test papers are sensitive to ultraviolet light, and the cover must therefore be opaque and remain closed until testing is desired and the fecal matter is smeared onto the test paper at the window openings. Hence, releasable locking structure in the form of a locking tab 40 on the back flap cover and a slotted opening 42 on the primary support sheet 12 serves to releasably lock the cover 36 to the support sheet 12.

Moreover, it is preferred that the strip of flexible material be opaque in order to protect the upper surface of the test paper from harmful ultraviolet degradation for the testing is performed. Aluminum foil or opaque plastic is particularly useful for this purpose.

The primary support sheet 12 and its associated back flap cover are preferably fabricated of cardboard to provide the necessary rigidity for manipulation and use of the testing device. Also, the transparent seal wrap 32 is preferably releasably heat sealed to the top of the second layer portion 26 around the outer boundary edge of the absorbent pad at 44. This seal is easily broken when the tab portion 24 is pulled but prior to using the device the heat seal 44 functions to prevent the absorbent pad from any unnecessary drying.

The testing device also includes a monitor 50 on the test paper 18 which provides a visual indication that the device is functioning in a proper manner. The monitor has a plus (+) portion 52 and a minus (−) portion 54. A solution containing an iron or lead compound, or heme (for example, a drop of blood in a pint of water) is applied to monitor portion 52 and allowed to dry prior to assembly of the device. Nothing is applied to monitor portion 54. When the device is used and the reaction liquid on the pad 30 is painted onto the monitor 50, the plus portion 52 turns blue due to the reaction between the hydrogen peroxide, the guaiac in the test paper, and the iron or lead compound or heme on portion 52. No discoloration should occur on minus portion 54. Hence, the monitor 50 provides a visual indication to the user of the device that it is operating in a proper manner.

What is claimed is:

1. A testing device for determining the presence of occult blood in fecal matter comprising a primary support sheet having top and bottom surfaces with at least one window opening therein for receiving fecal matter, a strip of test paper on the top surface of the primary support sheet covering the window opening, a strip of flexible material folded in two over the test paper including a first layer portion next to the test paper, a pull tab portion extending outwardly and away from the first layer portion past the primary support sheet, and a second layer portion next to the first layer portion terminating at a free inside end, an absorbent pad impregnated with reaction liquid secured to the strip of flexible material on top of the second layer portion, and a transparent seal wrap covering the layers of strip material and the absorbent pad, the seal wrap being secured to the top surface of the primary support sheet and the inside free end of the strip material whereby pulling the tab portion away from the primary support sheet draws the absorbent pad under the first and second layers of flexible material and across the test paper to thereby moisten the test paper covering the window opening with reaction liquid which turns the test paper a predetermined color when blood is present in the fecal matter.

2. A testing device as in claim 1 wherein the test paper includes gum guaiac resin and the reaction liquid includes hydrogen peroxide/alcohol.

3. A testing device as in claim 1 wherein the primary support sheet is cardboard.

4. A testing device as in claim 1 including an opaque back flap cover hingedly connected to the primary support sheet for covering the window opening before using the device.

5. A testing device as in claim 4 including releasable locking means on the back flap cover and the primary support sheet for releasably locking them together before using the device.

6. A testing device as in claim 4 wherein the support sheet and the back flap cover are cardboard.

7. A testing device as in claim 1 wherein the strip of flexible material is opaque.

8. A testing device as in claim 7 wherein the strip of opaque flexible material is aluminum foil.

9. A testing device as in claim 7 wherein the strip of opaque flexible material is opaque plastic.

10. A testing device as in claim 1 including a pair of spaced apart window openings in the support sheet.

11. A testing device as in claim 1 wherein the absorbent pad has an outer boundary edge and the transparent seal wrap is releasably heat sealed to the top of the second layer portion of strip material around the outer boundary edge of the pad.

12. A testing device as in claim 1 including a monitor on the test paper constructed and arranged to provide a visual indicator that the device is functioning in a proper manner.

* * * * *